United States Patent [19]

Ammann et al.

[11] Patent Number: 5,356,921
[45] Date of Patent: Oct. 18, 1994

[54] IMIDAZOLYLPHENOL COMPOUNDS, PHARMACEUTICAL COMPOSITIONS CONTAINING THEM, AND PROCESSES FOR PREPARING SUCH COMPOUNDS AND COMPOSITIONS

[75] Inventors: Joachim Ammann, Aachen; Michael Haurand, Stolberg; Cornelia Geist, Aachen; Werner Englberger, Stolberg; Oswald Zimmer, Wuerselen, all of Fed. Rep. of Germany

[73] Assignee: Gruenenthal GmbH, Aachen, Fed. Rep. of Germany

[21] Appl. No.: 19,193

[22] Filed: Feb. 17, 1993

[30] Foreign Application Priority Data

Feb. 17, 1992 [DE] Fed. Rep. of Germany ....... 4204686

[51] Int. Cl.$^5$ .................. A61K 31/535; C07D 233/60
[52] U.S. Cl. .................. 514/397; 514/399; 514/826; 548/315.1; 548/315.4; 548/338.1; 548/338.5
[58] Field of Search .............. 548/315.1, 315.4, 338.5, 548/338.1; 514/397, 399, 826

[56] References Cited

U.S. PATENT DOCUMENTS

| | | | |
|---|---|---|---|
| 3,950,333 | 4/1976 | Durant et al. | 544/224 |
| 4,581,369 | 4/1986 | Tsuruda et al. | 514/399 |
| 4,602,016 | 7/1986 | Cross et al. | 514/234 |
| 4,636,500 | 1/1987 | Cross et al. | 514/234 |
| 4,665,080 | 5/1987 | Wess et al. | 514/341 |

FOREIGN PATENT DOCUMENTS

| | | |
|---|---|---|
| 232954 | 8/1987 | European Pat. Off. |
| 0292699 | 11/1988 | European Pat. Off. |
| 384594 | 8/1990 | European Pat. Off. |
| 452908 | 10/1991 | European Pat. Off. |
| 2444031 | 7/1980 | France. |
| WO90/12008 | 10/1990 | PCT Int'l Appl. |

OTHER PUBLICATIONS

European Search Report, Den Haag, completed May 10, 1993.
Tai et al., "On the Inhibitory Potency of Imidazole and its Derivatives on Thrombboxane Synthetase", *Biochem. and Biophys. Res. Comm.*, vol. 80, No. 1, pp. 236–242 (1978).
Summers et al., "Orally Active Hydroxamic Acid Inhibitors of Leukotriene Biosynthesis", *J. Med. Chem.*, vol. 31, No. 1, pp. 3–5 (1988).
Tanaka et al., "Studies on Furan Derivatives, XII.", *J. Heterocyclic Chem.*, vol. 18, pp. 1241–1244 (1981).
Meerwein, *Methoden der Organischen Chemie*, Fourth Edition, vol. 6/3, pp. 85–90 Houben-Weyl, Stuttgart (1965).

*Primary Examiner*—Johann Richter
*Assistant Examiner*—Catherine S. Kilby Scalzo
*Attorney, Agent, or Firm*—Evenson, McKeown, Edwards & Lenahan

[57] ABSTRACT

3- and 4-(1H-imidazol-1-yl)phenol compounds corresponding to the formula I

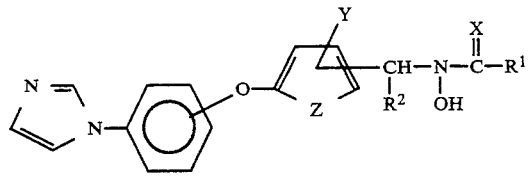

in which $R^1$ represents $NH_2$ or $CH_3$, $R^2$ represents H or $CH_3$, X represents O or S, Y represents H, OH or $OCH_3$, and Z represents —CH=CH—, O or S, or their salts, which exhibit 5-lipoxygenase and thromboxane synthase inhibiting activities.

16 Claims, No Drawings

IMIDAZOLYLPHENOL COMPOUNDS, PHARMACEUTICAL COMPOSITIONS CONTAINING THEM, AND PROCESSES FOR PREPARING SUCH COMPOUNDS AND COMPOSITIONS

BACKGROUND OF THE INVENTION

Polyunsaturated higher fatty acids such as arachidonic acid serve in the metabolism of mammals including humans as substrates for the formation of physiologically and pathophysiologically important eicosanoids such as prostaglandins, thromboxanes, prostacyclin and leukotrienes. The pathway to prostaglandins, thromboxanes and prostacyclin is initiated by cyclooxygenase whereas the pathway to leukotrienes is initiated by 5-lipoxygenase.

Thromboxane A2, a highly unstable and biologically active compound is extremely effective in inducing smooth muscle contraction as well as platelet aggregation. The formation of this compound from prostaglandin endoperoxides takes place in various cells such as human platelets and is catalyzed by thromboxane synthase (*Biochem. Biophys. Res. Commun.* 80, 236 (1978)). Some 1-substituted imidazoles are known which inhibit the activity of thromboxane synthase (also often named as thromboxane synthetase) resulting in an inhibiting effect on formation of thrombosis.

Leukotrienes play an important role in inflammatory and immune reactions and may cause life threatening situations for example anaphylactic or septic shock, allergic reactions, bronchoconstriction and asthma. Because of the harmful effects of leukotrienes, numerous compounds have been investigated with regard to their inhibiting effect on 5-lipoxygenase. In Summers et al., Published European Patent Application No. EP 292,699 and Brooks et al., Published PCT Patent Applications No. WO 90/12008, for example, substituted phenyl, naphthyl and thienyl N-hydroxy urea compounds are disclosed, Which are suitable as inhibitors of 5-lipoxygenase.

To date, no compound is known which inhibits the activity of 5-lipoxygenase and thromboxane synthase simultaneously. This means that two active substances have to be administered if both enzymes (5-lipoxygenase and thromboxane synthase) have to be inhibited. There remains a need for a single active compound which can inhibit the actions of both 5-lipoxygenase and thromboxane synthase.

SUMMARY OF THE INVENTION

It is therefore the object of the invention to provide stable and toxicologically acceptable compounds which inhibit the activity of 5-lipoxygenase and thromboxane synthase simultaneously.

It is also an object of the invention to provide pharmaceutical compositions which can inhibit the activity of 5-lipoxygenase and thromboxane synthase simultaneously.

A further object of the invention is to provide compounds and pharmaceutical compositions which can be used in the treatment of asthma.

Another object of the invention to provide a method of treating a patient suffering from a disorder attributable to the action of leukotrienes and thromboxane A2.

These and other objects of the invention are achieved in accordance with the present invention by providing a 3- or 4-(1H-imidazol-1-yl)phenol compound corresponding to the formula I

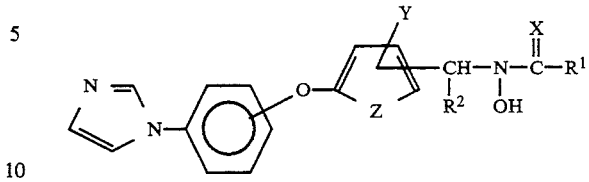

wherein $R^1$ represents $NH_2$ or $CH_3$; $R^2$; represents H or $CH_3$; X represents O or S; Y represents H, OH or $OCH_3$, and Z represents —CH=CH—, O or S; or a pharmaceutically acceptable salt thereof.

In accordance with a further aspect of the invention, the objects are achieved by providing a pharmaceutical composition comprising an effective 5-lipoxygenase and thromboxane synthase inhibiting amount of at least one 3- or 4-(1H-imidazol-1-yl)phenol compound as defined above and a pharmaceutically acceptable carrier, diluent or solvent.

DETAILED DESCRIPTION OF PREFERRED EMBODIMENTS

It now has been found that certain imidazolylphenol derivatives inhibit the activity of 5-lipoxygenase as well as the activity of thromboxane synthase.

Accordingly the present invention relates to 3- or 4-(1H-imidazol-1-yl)phenol derivatives of formula I

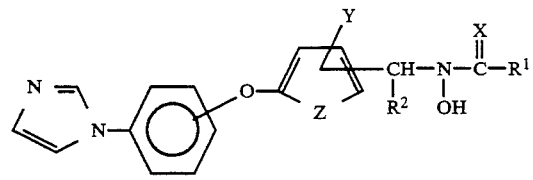

in which $R^1$ represents $NH_2$ or $CH_3$, $R^2$ represents H or $CH_3$, X represents O or S, Y represents H, OH or $OCH_3$, and Z represents —CH=CH—, O or S, or their salts.

Compounds of formula I in which $R^2$ is the methyl group have one asymmetric center. Accordingly the invention also relates to racemates as well as to the optically active forms of the compounds of formula I.

The residues Y and

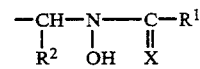

in the phenyl-, thienyl- or furanyl residue may be in any position.

Imidazolylphenol derivatives Or the salts thereof in which $R^2$ represents H are preferred. Imidazolylphenol derivatives or their salts, in which Z represents —CH=CH—, especially N-hydroxy-N-[4-[4-(1H-imidazol-1-yl)phenoxy]phenylmethyl]urea, the imidazolium chloride of this compound, N-hydroxy-N-[4-[4-(1H-imidazol-1-yl)phenoxy]phenylmethyl]acetamide, N-hydroxy-N-[3-[4-(1H-imidazol-1-yl)phenoxy]phenylmethyl]urea, N-hydroxy-N-[3-[4-(1H-imidazol-1-yl)phenoxy]-6-methoxy-phenylmethyl]urea, N-hydroxy-N-{1-[4-[4-(1H-imidazol-1-yl)phenoxy]phenyl]ethyl}urea, N-hydroxy-N-[4-[4-(1H-imidazol-1-yl)phenoxy]phenylmethyl]thiourea, and N-hydroxy-N-

[4-[3-(1H-imidazol-1-yl)phenoxy]phenylmethyl]urea, imidazolylphenol derivatives or their salts in which Z represents S, especially N-hydroxy-N-[5-[4-(1H-imidazol-1-yl)phenoxy]thien-2-yl-methyl]urea, and imidazolylphenol derivatives or their salts in which Z represents O, especially N-hydroxy-N-[5-[4-(1H-imidazol-1-yl)phenoxy]furan-2-yl-methyl]urea are particularly preferred compounds.

The imidazolylphenol derivatives or the salts thereof selectively inhibit the activity of 5-lipoxygenase and thromboxane synthase but have no effect on the activity of 12-lipoxygenase and cyclooxygenase. Due to their selective inhibitory action on 5-lipoxygenase and thromboxanesynthase and thus on production of metabolites of arachidonic acid such as 5-hydroxyeicosatetraenoic acid (5-HETE), $LTB_4$, $LTC_4$, $LTD_4$, $LTE_4$ and thromboxane A2, the compounds according to the invention exhibit various physiologically valuable properties such as anti-thrombotic, anti-vasospastic, antivasoconstricting, aggregation inhibiting, anti-anaphylactic, anti-asthmatic, anti-allergic, anti-phlogistic, blood pressure lowering, cerebral- and coronary-circulation improving as well as anti-psoriatic effects. Further the compounds according to the invention inhibit the activation, the aggregation as well as the consumption of thrombocytes and leucocytes, the activation of macrophages such as alveolear macrophages and copper cells as well as the activation of smooth muscle cells in tissue veins and arteries. Due to their chemical stability and to their metabolic stability when used as a therapeutic agent, the imidazolylphenol derivatives of formula I or their salts are suitable for use as a medicament such as an inhibiting agent for the aggregation of thrombocytes, a vasodilatator, an anti-allergic, anti-anaphylactic, anti-phlogistic, anti-asthmatic and anti-hypertensive agent, an agent for use in treatment or prophylaxis of ischemic myocardial infarction, or an agent for use in treatment of disorders of coronary and/or cerebral blood vessels.

The imidazolylphenol derivatives or their salts have a low degree of toxicity. Accordingly these compounds may be administered to humans and animals in form of suitable pharmaceutical compositions.

The invention also relates to medicaments containing as active ingredient at least one imidazolylphenol derivative of formula I or at least one salt thereof. The dosage of this active ingredient to be administered to a patient depends on the body weight, on the form and manner of administration, on the nature of the clinical indication, and on the state of disease in the individual to be treated. In consideration of these factors, in general a unit dose form of a medicament according to the invention will contain from about 0.01 to about 1000 mg of the active ingredient, whereby compositions for parenteral administration preferably contain about 0.1 to about 1000 mg, compositions for topical or inhalative administration preferably contain about 0.01 to about 100 mg, and compositions for oral administration preferably contain about 1 to about 1000 mg of the active ingredient.

Due to their high solubility in water, the salts of imidazolylphenol derivatives of formula I are especially useful for topical, inhalative and parenteral administration. Solutions, suspensions and dry formulations suitable for easy reconstitution are very useful for these application forms. Sprays are also suitable for topical and inhalative administration.

Compositions for oral administration such as tablets, dragees, capsules, granules, drops and syrups are very suitable for prophylactic or therapeutic administration of the compounds of formula I in many cases, as well as suppositories or compositions for percutaneous administration, for example the active ingredient in a plaster or the like, in a solution, optionally with the addition of a known skin penetration enhancing agent. Advantageously these orally, rectally or percutaneously administrable forms are produced in such a way that the active ingredient is released therefrom in a delayed fashion in order to assure a uniform supply of the active ingredient to the patient over an extended period of time, for example 24 hours.

All of the foregoing general types of pharmaceutical compositions to which the invention is applicable as well as the preparation of these compositions are known. Since the compounds of formula I are chemically stable, their incorporation into these pharmaceutical compositions in the form and dosage desired poses no problems for an ordinarily skilled pharmacist. In the production of pharmaceutical compositions according to the invention, the usual care must naturally be taken in the selection of inorganic or organic adjuvants such as carriers, diluents, solvents, binders, tablet disintegrating agents, coloring agents, and flavorings. In particular in the production of compositions for parentral administration, care should be taken to achieve sterility and if the compositions are in liquid form, isotonicity.

A further object of the invention is a process for preparing a 3- or 4-(1H-imidazol-1-yl)phenol derivative of formula I

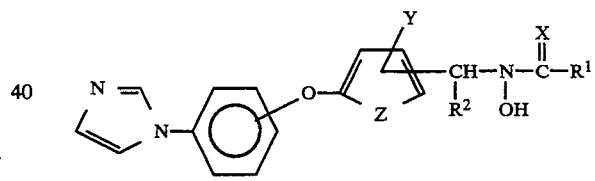

in which $R^1$ represents $NH_2$ or $CH_3$, $R^2$ represents H or $CH_3$, X represents O or S, Y represents H, OH or $OCH_3$, and Z represents —CH=CH—, O or S, or a salt thereof, said process comprising the steps of reacting a carbonyl compound of formula II $R^3$-Aryl in which $R^3$ represents a halogen, $NO_2$ or OH, and in which aryl represents

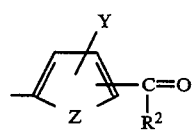

with 3-(1H-imidazol-1-yl) phenol or 4-(1H-imidazol-1-yl)phenol or an alkali salt thereof in the presence of a solvent and optionally in presence of a catalytic amount of copper and/or a copper-I-salt and, if $R^3$ represents OH, after reaction with a sulfochloride to form a compound of formula III

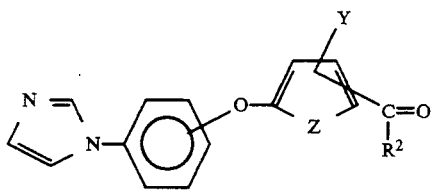

reacting the compound of formula III with hydroxyl amine or a salt thereof in the presence or absence of a base and in the presence of a solvent to form the oxime of formula IV

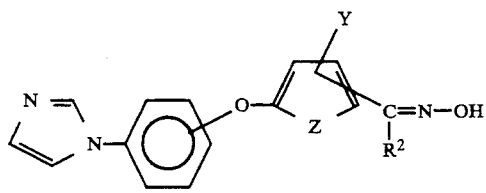

reducing the resulting oxime with a borane-containing reducing agent in the presence of an acid to a hydroxylamine of formula V

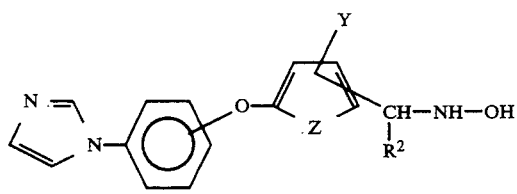

transforming the resulting hydroxylamine into the imidazolylphenol derivative of formula I by
(A) reaction with an alkali cyanate or an alkali thiocyanate, or
(B) reaction with trimethylsilyl isocyanate or trimethylsilyl isothiocyanate, followed by splitting off the trimethylsilyl group, or
(C) reaction with an acetylating agent followed by treatment with a base to split off the O-acetyl group of the resulting bis-acetyl compound,
and optionally converting the resulting imidazolylphenol derivative of formula I with an acid into a corresponding salt.

Compounds of formula III are preferably prepared by reacting a carbonyl compound of formula II R³-Aryl in which R³ represents Cl, Br or I, and aryl represents

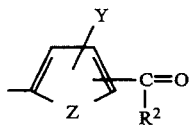

For this purpose 3-(1H-imidazol-1-yl)phenol or 4-(1H-imidazol-1-yl)phenol, optionally diluted in a polar solvent or solvent mixture, is converted with 1 to 5 equivalents of one or more bases, such as sodium and/or potassium hydroxide, sodium and/or potassium carbonate and/or sodium alcoholate, e.g. sodium methylate, into the corresponding alkali salt, and then in the presence of a polar solvent or solvent mixture and in the presence of a catalytic amount of activated copper powder and/or copper-I-salts such as copper-I-halogenides, after addition of a carbonyl compound of formula II in an amount of about 1 to 2 equivalents [based on charged (1H-imidazol-1-yl)phenol] heated at a temperature between 50° and 160° C. Suitable polar solvents include dimethyl sulfoxide, dimethyl formamide, alcohols such as methanol or ethanol, tetrahydrofuran, and 1,4-dioxane. Dimethyl sulfoxide and/or dimethyl formamide are preferably used [H. Meerwein in Methoden der organischen Chemie, Houben-Weyl, 4th Edition, Vol. 6/3, pages 85–89, Stuttgart (1965)].

Alternatively a compound of formula III may be prepared by transforming 3-(1H-imidazol-1-yl)phenol or 4-(1H-imidazol-1-yl)phenol with one of the above mentioned bases in the presence of one or more of the polar solvents mentioned above, into the corresponding alkali metal salt and reacting the resulting salt with 0.9 to 1.0 equivalents of a carbonyl compound of formula II R³-Aryl wherein R³ is NO₂ and aryl is

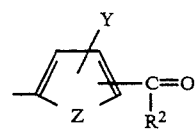

at a temperature between 40° and 160° C. [J. Heterocyclic Chem. 18, 1241 (1981)].

Another method of preparing a compound of formula III is the reaction of a carbonyl compound of formula II R³-Aryl in which R³ is OH and aryl is

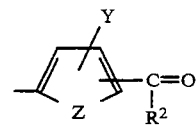

diluted in a tertiary amine, especially pyridine, with about 1 to 2 equivalents of a sulfochloride such as benzene-, toluene-, methane- or trifluoromethane-sulfonyl chloride, resulting in the corresponding sulfonate which is then reacted with one equivalent of 3-(1H-imidazol-1-yl)phenol or 4-(1H-imidazol-1-yl)phenol to form a compound of formula III [H. Meerwein in Methoden der orgahischen Chemie, Houben-Weyl, 4th Edition, Vol. 6/3, pages 89–90, Stuttgart (1965)].

To prepare oximes of formula IV, a compound of formula III

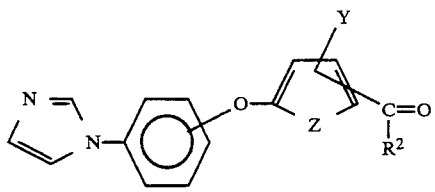

in which R² preferably is H; Y is H, OH or OCH₃; and Z is —CH═CH—, O or S, may be reacted in a known manner with 1 to 2 equivalents of hydroxylamine and/or a salt thereof, such as hydroxylamine hydrochloride, in a polar solvent or solvent mixture, for example methanol, ethanol, tetrahydrofuran and/or pyridine and in presence of one or more bases, e.g. pyridine, triethylamine, alkali alcoholate such as sodium methylate, potassium tert.-butylate, potassium and/or sodium carbonate and/or sodium acetate at a temperature between 18° and 25° C. Then the resulting oxime is reduced to the hydroxylamine of formula V with a borane-containing reducing agent especially a borane-amine complex, e.g. borane-pyridine complex, or borane-tetrahydrofuran complex in a polar solvent or solvent mixture such as alkyl alcohols, e.g. methanol, ethanol, tetrahydrofuran or 1,4-dioxane in the presence of one or more acids such as hydrochloric acid or acetic acid at temperatures of 0° to 5° C. [J. B. Stammers et al., *J. Med. Chem.*, 31, 1960 (1988)].

To prepare 3- or 4-(1H-imidazol-1-yl)phenol derivatives of formula I in which $R^1$ is $NH_2$, a hydroxylamine of formula V may be reacted, without isolation from the reaction mixture in which it was prepared, with 1 to 6 equivalents of an alkali cyanate or an alkali thiocyanate such as potassium cyanate or potassium thiocyanate. Alternatively the compounds of formula I may be obtained by reacting a hydroxylamine of formula V after isolation from the reaction mixture in which it was prepared with 1 to 1.4 equivalents of trimethylsilyl isocyanate or trimethylsilyl isothiocyanate in aprotic solvents such as cyclic ethers, e.g. tetrahydrofuran or 1,4-dioxane, dimethyl sulfoxide and dimethyl formamide at temperatures of 20° to 80° C. The resulting intermediate then is hydrolyzed, e.g. by treatment with the saturated aqueous solution of ammonium chloride, to obtain the desired compound of formula I.

To prepare imidazolylphenol derivatives of formula I in which $R^1$ is $CH_3$, a hydroxylamine of formula V, optionally without isolation from the reaction mixture in which it was prepared, is reacted with an acetylating agent, preferably acetic anhydride, ethyl acetate or acetyl chloride, to obtain the corresponding bis-acetyl compound from which the O-acetyl group is split off by treatment with a base in the presence of an alcoholic solvent, e.g. methanol, ethanol or isopropanol, at temperatures of 20° to 60° C. Suitable bases include, for example, lithium, sodium or potassium hydroxide, or sodium or potassium carbonate, which optionally may be added in the form of an aqueous solution.

The imidazolylphenol derivatives of formula i may be transformed into corresponding salts by adding at least an equimolar amount of one or more acids such as hydrochloric acid or sulfuric acid, to an aqueous suspension of the imidazolylphenol derivative. The resulting salts may be precipitated in presence of acetone and crystallized from ethanol or isolated by freeze drying.

EXAMPLES

All temperature references are uncorrected. The $^1$H-nuclear magnetic spectra ($^1$H-NMR) were measured at 300 MHz. The chemical shifts are given in ppm. In column chromatography, silica gel ("Kieselgel 60", 0.063 to 0.200 mm corresponding to 70 to 230 mesh ASTM from E. Merck of Darmstadt, Germany) was used as the stationary phase. Copper powder was activated according to the method described in *Org. Synthesis, Coil.* Vol. II, 446.

Example 1

N-hydroxy-N-[4-[4-(1H-imidazol-1-yl)phenoxy]phenylmethyl]urea a) 4-[4-(1H-imidazol-1-yl)phenoxy]benzaldehyde A suspension of 40.04 g (0.25 mole) of 4-(1H-imidazol-1-yl)phenol, 15.2 g (0.11 mole) of anhydrous potassium carbonate, 1 g of copper-I-bromide, and 0.5 g of activated copper powder in 100 ml of anhydrous dimethyl formamide was heated to 90° C. Over the course of 7 hours 47.03g (0.25 mole) of 4-bromobenzaldehyde were added in small portions to the suspension while the mixture was heated to 140° to 145° C. After the addition of the aldehyde was completed, the mixture was allowed to cool. Then 1500 ml of ice-cooled ethyl acetate were added to the reaction mixture. The resulting mixture was shaken with 500 ml of 1N aqueous sodium hydroxide solution. After separation of undissolved ingredients, the organic layer was shaken with 1N aqueous sodium hydroxide solution and washed with a saturated aqueous sodium chloride solution. After drying over magnesium sulfate, the drying agent was separated and the resulting filtrate evaporated at 45° C. and $2.6 \times 10^3$ to $6 \times 10^3$ Pa. After column chromatography with ethyl acetate, 37.37 g (56.6% of the theoretical yield) of the aldehyde were obtained in the form of yellow brown crystals melting at 120° to 121° C.

$^1$H-NMR (DMSO-d$_6$): 7.14–7.18 (m, $^1$H, aromat.); 7.29–7.32 (m, 2H, aromat.); 7.74–7.77 (m, 3H, aromat.); 7.94–7.96 (m, 2H, aromat.), 8.26 (s, 1H, aromat.); 9.95 (s, 1H, CHO).

b) N-Hydroxy-N-[4-[4-(1H-imidazol-1-yl)phenoxy]-phenylmethyl]urea

To 0.9 g (13 mmole) of hydroxylamine hydrochloride in 9 ml of anhydrous methanol were added 13 ml of 1N methanolic solution of sodium methylate and then a solution of 2.64 g (10mmole) of the aldehyde prepared according to Example 1a) in 19 ml of anhydrous methanol. After stirring for one hour at 20° C., the reaction mixture was cooled in an ice bath. After addition of 4 ml (40 mmole) of borane-pyridine complex, the mixture was stirred at 0° C. for 2 hours. Then 5.3 ml (63 mmole) and after an additional hour 3.3 ml (30 mmole) of concentrated hydrochloric acid were added. After 24 hours at +4° C. 5 ml of 10N sodium hydroxide solution were added resulting in a pH-value of 6 in the mixture. Then a solution of 4.9 g (60 mmole) of potassium cyanate in 10 ml of water was added dropwise. After 5.5 hours at 20° C., the mixture was evaporated at 45° C. and $1.5 \times 10^3$ Pa. The resulting residue was dissolved in a mixture of 50 ml of tetrahydrofuran and 70 ml of ethyl acetate and shaken with a 0.1N sodium hydroxide solution and then with a saturated aqueous solution of sodium chloride. After drying over magnesium sulfate, separating the drying agent and adding toluene, the solvent was evaporated at 45° C. and $2.6 \times 10^3$ to $6 \times 10^3$ Pa. The resulting residue was dried at a pressure of <13 Pa and recrystallized from a mixture of 15 ml of methanol and 9 ml of anhydrous diethyl ether to yield 2.18 g (67.2% of the theoretical yield)of N-hydroxy-N-[4-[4(1H-imidazol-1-yl)phenoxy]phenylmethyl]urea in the form of colorless crystals melting at 159° C.

$^1$H-NMR (DMSO-d$_6$): 4.52 (s, 2H, CH$_2$); 6.35 (S, 2H, NH$_2$); 6.99–7.10 (q, 2H, aromat.); 7.13–7.14 (m, 3H, aromat.); 7.32–7.34 (q, 2H, aromat.); 7.61–7.65 (m, 3H, aromat.); 8.16 (s, 1H, aromat.); 9.37 (s, 1H, OH).

Example 2

Imidazolium Chloride of N-hydroxy-N-[4-[4-(1H-imidazol-1-yl)phenoxy]phenylmethyl]urea 3.24 g (10 mmole) of N-hydroxy-N-[4-[4-(1H-imidazol-1-yl)phenoxy]phenylmethyl]urea were suspended in 10 ml of water and diluted by addition of 1.7 ml of 6N hydrochloric acid. The imidazolium chloride was precipitated by addition of 150 ml of acetone, washed with acetone, and recrystallized from 150 ml of anhydrous ethanol to yield 2.85 g (80% of the theoretical yield) of the imidazolium chloride decomposing at 156° C.

$^1$H-NMR (DMSO-$d_6$): 4.54 (s, 2H, CH$_2$); 6.37 (s, 1H, NH$_2$); 7.03–7.19 (q, 2H, aromat.); 7.20–7.38 (q, 2H, aromat.); 7.80–7.84 (m, 2H, aromat.); 7.90–7.91 (t, 2H, aromat.); 8.25–8.26 (t, 1H, aromat.); 8.33 (d, 1H, aromat.); 9.45 (s, 1H, OH); 9.75 (s, 1H, aromat.); ca. 16 (s, broad, 1H+, aromat.).

Example 3

N-hydroxy-N-[4-[4-(1H-imidazol-1-yl)phenoxy]phenylmethyl]acetamide

Concentrated hydrochloric acid was added to the hydroxylamine prepared according to Example 1. After evaporation of methanol at 45° C. and $2.6 \times 10^3$ to $6 \times 10^3$ Pa, an equal volume of ethyl acetate was added to the aqueous residue obtained from the methanol evaporation. Then the mixture was allowed to cool in an ice bath, and the pH was adjusted to 10 by addition of an aqueous 10N solution of sodium hydroxide. The precipitated oil was extracted with ethyl acetate, and the resulting extract was dried over magnesium sulfate and after addition of toluene evaporated at 45° C. and $1.5 \times 10^3$ Pa and then dried at 40° C. and 13 Pa. 2.95 g (10.5 mmole) of the resulting residue were dissolved in 80 ml of anhydrous tetrahydrofuran. To the resulting solution were added 5.15 ml (37 mmole) of triethylamine and then 2.76 ml (36.2 mmole) of acetyl chloride diluted in 20 ml of anhydrous tetrahydrofuran while stirring at 0° C. After one-half hour the reaction mixture was evaporated at $4 \times 10^3$ Pa; the resulting residue was dissolved in 20 ml of anhydrous methanol and after addition of 100 ml of water extracted with ethyl acetate. After drying and evaporating of the extract at 45° C. and $4 \times 10^3$ Pa, 7.28 g of a yellow oil were obtained which were diluted in 70 ml of isopropanol and after addition of a solution of 1.5 g of lithium hydroxide in 15 ml of water saponified at 40° C. over the course of three hours. After addition of 200 ml of water, the pH was adjusted to a value of 7, and the mixture was extracted with ethyl acetate. After drying over magnesium sulfate and evaporating the extract, 5.95 g of a solid light yellow residue were obtained which were purified by column chromatography with tetrahydrofuran to yield 3.17 g of N-hydroxy-N-[4-[4-(1H-imidazol-1-yl) phenoxy] phenylmethyl]acetamide in the form of pale yellow crystals melting at 149° C.

$^1$H-NMR (DMSO-$d_6$): 2.05 (s, 3H, CH$_3$); 4.67 (s, 2H, CH$_2$); 7.01–7.04 (q, $^1$H, aromat.); 7.09–7.15 (m, 3H, aromat.); 7.29–7.32 (q, 2H, aromat.); 7.61–7.67 (m, 3H, aromat.); 8.17 (s, 1H, aromat.); 9.89 (s, 1H, OH).

Example 4

N-hydroxy-N-[5-[4-(1H-imidazol-1-yl)phenoxy]thien-2-yl-methyl]urea.

The urea compound was prepared from 47.8 g (0.25 mole) of 5-bromothiophene-2-aldehyde according to Example 1.

Melting point: 141° C.

$^1$H -NMR (DMSO -$d_6$ ): 4.56 (s, 2H, CH$_2$); 6.44 (s, 2H, NH$_2$); 6.52–6.54 (d, 1H, aromat.); 6.76–6.77 (d, 1H, aromat.); 7.09 (s, 1H, aromat.); 7.22–7.25 (m, 2H, aromat.); 7.63–7.67 (m, 3H, aromat.); 8.18 (s, 1H, aromat.); 9.5–10.0 (s, broad, 1H, OH ).

EXAMPLE 5

N-hydroxy-N-[3-[4-(1H-imidazol-1-yl)phenoxy]phenylmethyl]urea

The urea compound was prepared from 46.3 g (0.25 mole) of 3-bromobenzaldehyde according to Example 1.

Melting point: 163° C.

$^1$H-NMR (DMSO-$d_6$): 4.53 (s, 2H, CH$_2$); 6.39 (s, 2H, NH$_2$); 6.91–6.95 (q, 1H, aromat.); 7.01–7.09 (d, 1H, aromat.); 7.11–7.15 (m, 4H, aromat.); 7.33–7.38 (t, 1H, aromat.); 7.62–7.67 (m, 3H, aromat.); 8.18 (s, 1H, aromat.); 9.43 (s, 1H, OH).

Example 6

N-hydroxy-N-[5-[4-(1H-imidazol-1-yl)phenoxy]furan-2-yl-methyl]urea

The urea compound was prepared from 35.3 g (0.25 mole) of 5-nitrofuran-2-aldehyde according to Example 1, but using neither copper-I-bromide nor copper powder.

Melting point: 155° C.

$^1$H-NMR (DMSO-$d_6$): 4.42 (s, 2H, CH$_2$); 5.75–5.76 (d, 1H, aromat.); 6.30–6.31 (d, 1H, aromat.); 6.44 (s, 2H, NH$_2$); 7.09 (s, 1H, aromat.); 7.16–7.22 (m, 2H, aromat.); 7.62–7.67 (m, 3H, aromat.); 8.18 (s, 1H, aromat.); 9.44 (s, 1H, OH).

Example 7

N-hydroxy-N-[3-[4-(1H-imidazol-1-yl)phenoxy]-6-methoxyphenylmethyl]urea.

The urea compound was prepared from 54.3 g (0.25 mole) of 3-bromo-6-methoxybenzaldehyde according to Example 1.

Melting point: 111° C.

$^1$H-NMR (DMSO-$d_6$): 3.80 (s, 3H, OCH$_3$); 4.56 (s, 2H, CH$_2$); 6.41 (s, 2H, NH$_2$); 6.93–7.08 (m, 6H, aromat.); 7.55–7.63 (m, 3H, aromat.); 8.14 (s, 1H, aromat.); 9.50 (s, 1H, OH).

Example 8

N-hydroxy-N-{1-[4-[4-(1H-imidazol-1-yl)phenoxy]-phenyl]ethyl}urea

Following the procedure described in Example 1, but using 49.8 g (0.25 mole) of 4-bromoacetophenone, the urea compound was obtained in the form of colorless crystals melting at 160° C.

$^1$H-NMR (DMSO-$d_6$): 1.41–1.43 (d, 3H, CH$_3$); 5.28–5.36 (m, 1H, CH); 6.28 (s, 2H, NH$_2$) 6.90–7.16 (m, 5H, aromat.); 7.32–7.43 (d, 2H, aromat.); 7.52–7.68 (m, 3H, aromat.); 8.15 (s, 1H, aromat.); 9.07 (s, 1H, OH).

Example 9

N-hydroxy-N-[4-[4-(1H-imidazol-1-yl)phenoxy]phenyl-methyl]thiourea

The hydroxylamine obtained by reduction of the oxime with borane-pyridine complex according to Example 1 was isolated and dissolved in 25 ml of 1,4-dioxane. To the resulting solution were added 1.7ml of trimethylsilyl isothiocyanate while stirring at 20° C. After 3 hours the reaction mixture was shaken with a saturated aqueous solution of ammonium chloride and then with a saturated aqueous solution of sodium chloride. The resulting organic layer then was dried over sodium sulfate, the mixture was evaporated, and the residue was recrystallized from a mixture of 1,4-dioxane/water to yield 1.92 g (56.4% of the theoretical yield) of N-hydroxy-N-[4-[4-(1H-imidazol-1-yl)phenoxy]phenyl]-methylthiourea in the form of colorless crystals which melted with decomposition at 174° C.

$^1$H-NMR (DMSO-d$_6$): 5.22 (s, 2H, CH$_2$); 7.02–7.15 (m, 5H, aromat.); 7.41–7.44 (d, 2H, aromat.); 7.62–7.69 (m, 3H, aromat.); 8.22 (s, 1H, aromat.); 10.08 (s, 1H, OH).

Example 10

N-hydroxy-N-[4-[3-(1H-imidazol-1-yl)phenoxy]phenyl-methyl]urea

Following the procedure described in Example 1, but using 3-(1H-imidazol-1-yl)phenol, the urea compound was obtained in form of colorless crystals melting at 158° C.

$^1$H-NMR (DMSO-d$_6$): 4.54 (s, 2H, CH$_2$); 6.37 (s, 2H, NH$_2$); 6.85–6.89 (d, 1H aromat.); 7.00–7.10 (m, 3H, aromat.); 7.30–7.48 (m, 5H, aromat.); 7.71 (s, 1H, aromat.); 8.24 (s, 1H, aromat.); 9.42 (s, 1H, OH).

Comparison Example

N-hydroxy-N-[4-[2-(1H-imidazol-1-yl)ethoxy]phenyl-methyl]urea 6.11 g (0.05 mole) of 4-hydroxybenzaldehyde were diluted in 100 ml of anhydrous dimethyl formamide and transformed into the sodium salt with 2.4 g (one equivalent) of a dispersion of 50% by weight sodium hydroxide in paraffin oil. To the resulting suspension were added 376 g (2 moles) of 1,2-dibromoethane. After boiling under reflux for 2 hours, the mixture was allowed to cool to 20° C. and separated from salts and dimethyl formamide by extraction with water. After evaporation of excess 1,2-dibromoethane at 1.5×10$^3$ Pa, a suspension of sodium imidazolide, prepared from 885 mg imidazole and 624 mg of a dispersion of 50% by weight sodium hydride in paraffin oil and suspended in 20 ml anhydrous dimethyl formamide, was added to the residue obtained. After 5.5 hours at 100° C. the reaction mixture was poured into ice water, acidified and extracted with dichloromethane to remove the paraffin oil. After adjustment to a pH-value of 9, the resulting 4-[2-(1H-imidazol-1-yl)ethoxy]benzaldehyde was extracted with dichloromethane. After evaporation of the solvent, 2.14 g of the benzaldehyde were obtained in the form of a yellow oil. In accordance with Example 1 the benzaldehyde obtained was converted into the oxime which was reduced to the corresponding hydroxylamine from which N-hydroxy-N-[4-[2-(1H-imidazol-1-yl)ethoxy]phenylmethyl]urea was obtained which decomposed at 155° C.

$^1$H-NMR (DMSO-d$_6$): 4.19–4.36 (m, 4H, CH$_2$CH$_2$); 4.43 (s, 2H, CH$_2$N); 6.31 (s, 2H, NH$_2$); 6.85–6.88 (m, 3H, aromat.); 7.18–7.23 (m, 3H, aromat.); 7.67 (s, 1H, aromat.); 9.32 (s, 1H, OH).

Biological Investigations

All listed IC$_{50}$-values are absolute values. In thin layer chromatography, silica gel Si 60 from E. Merck of Darmstadt, Germany was used as the stationary phase. RP-HPLC means reverse-phase-high-pressure-liquid chromatography. TXB$_2$ means thromboxane B$_2$, HETE means hydroxyeicosatetraenoic acid.

Inhibition of 5-lipoxygenase

1. Inhibition of 5-lipoxygenase in RBL-1-cells

To determine the inhibition of 5-lipoxygenase rat basophilic leukemia cells (RBL-1-cells) were cultured in vitro, harvested by centrifugation, washed with 50 mM potassium phosphate buffer of pH 7.4, and then suspended in this buffer at 1×10$^7$ cells/mi. To 1 ml each of this suspension there was added indomethacin (10 μM) and calcium chloride (2 mM), and then the mixture was incubated in the absence or presence of a compound according to the invention in a concentration range of from 0.1 μM to 100 μM for 3 minutes and thereafter with 20 μM of [$^{14}$C]-arachidonic acid and 20 μM of the calcium ionophore A 23 187 for 10 minutes. The reaction was stopped by adding 20 μl of glacial acetic acid, and then the mixture was extracted with ethyl acetate to isolate the metabolites of arachidonic acid formed by the enzymatic action of 5-lipoxygenase. These were separated by thin layer chromatography using a solvent mixture known to be suitable for lipoxygenase products [c.f. Jakschik et al., *Biochem. Biophys. Res. Commun.* 102, 624 (1981)].

The distribution of the radioactivity among the various metabolites of arachidonic acid was measured using a TLC Linear Analyzer. By correlating the percentages of the amount of the products formed under the action of 5lipoxygenase (5-HETE, isomers of LTB$_4$) in the absence as well as in the presence of different concentrations of compounds according to the invention, the IC$_{50}$-values, i.e. the concentrations which cause 50% inhibition of 5-lipoxygenase were determined graphically from semilogarithmic diagrams. The results are summarized in the following table:

| Compound According to Example No. | IC$_{50}$-Value [μm] |
|---|---|
| 1 | 2 |
| 2 | 5 |
| 3 | 5 |
| 4 | 3 |
| 5 | 6 |
| 10 | 2 |
| Comparison | >100 |

2. Inhibition of cell-free 5-lipoxygenase from RBL-1-cells

Cell-free 5-lipoxygenase was polarographically measured from 10,000×g supernatant of homogenized rat basophilic leucemia cells [M. Haurand and L. Flohé in *Biol. Chem. Hoppe-Seyler* 369, 133–142 (1988)]. After preincubation of the 10,000×g supernatant with arachidonic acid (75 μM), ATP (adenosine triphosphate; 4 μM), reduced glutathione (4 mM), and either a compound according to the invention (0.1 to 100 μM) or a solvent (ethanol and/or dimethyl sulfoxide) at 35° C.

for 5 minutes, the lipoxygenase reaction was initiated by addition of calcium chloride (3 mM) and recorded simultaneously.

The activity of 5-lipoxygenase was determined from the difference of the $pO_2$-decrease before and after addition of calcium chloride. The evaluation included the initial rate of the reaction after the lag-phase as well as the duration of the lag-phase. In a concentration range of from 5 to 10 μM the test substances induced lag-phases of 15 seconds. The determined $IC_{50}$-values are summarized in the following table:

| Compound According to Example No. | $IC_{50}$-Value [μm] |
|---|---|
| 1 | 7 |
| 3 | 3 |
| 5 | 2 |
| Comparison | >100 |

3. 5-lipoxygenase Inhibition in Rat Blood after Oral Administration

The bioavailability of the compounds of formula I as 5-lipoxygenase inhibitors was characterized by means of an ex vivo biochemical assessment method described by Tateson et al. in Brit. J. Pharmacol. 94, 528 (1988). A compound of formula I was orally administered to male rats (Wistar strain) in a dose of 21.5 mg/kg. One hour after administration the rats after lethal $CO_2$-narcosis were bled by heart puncture with added heparin as an anticoagulant. Aliquots of the whole blood were incubated at 37° C. for 30 minutes in a water bath with calcium ionophore A 23 187 at an end concentration of 15 μg/ml. At the end of the incubation the samples were centrifuged, and the concentration of immunoreactive $LTB_4$($iLTB_4$) in aliquots of ($^3H$-$LTB_4$-RIA, Amersham). To enable calculation of cell-free plasma was determined by radioimmunoassay percent inhibition of ex vivo $iLTB_4$-formation in whole blood of rats treated with a compound according to the invention, rats orally treated with an appropriate vehicle solution were included in all experiments, and aliquots of their blood were run in parallel and were processed in the same way as described. The average $iLTB_4$-content of the plasma of the vehicle treated rats served as the 100% value. The activity in percent of the ex vivo $iLTB_4$-formation after oral administration of a compound according to the invention was calculated by dividing the average value of the $iLTB_4$-content in ng $iLTB_4$/ml of the group treated with a compound according to the invention by the average value of the $iLTB_4$-contents in ng $iLTB_4$/ml of the vehicle treated group and subsequent multiplication by the factor 100. The respective inhibition in percent was calculated by subtracting the activity in percent from 100. The following table shows the resulting inhibition values after oral administration of 21.5 mg/kg of compounds according to the invention:

| Compound According to Example No. | Inhibition [%] |
|---|---|
| 1 | 89 |
| 2 | 95 |
| 3 | 91 |
| 4 | 93 |
| 6 | 84 |
| Comparison | 42 |

Inhibition of Leukotriene-Synthesis Induced by FMLP/Merthiolate of Human Polymorphonuclear Leukocytes Human granulocytes were isolated by dextran-sedimentation and a Percoll gradient method and suspended in HBSS (Hanks buffered salt solution) at $1 \times 10^7$ cells/mi. The cells were incubated in presence of a compound according to the invention or a solvent (ethanol and/or dimethyl sulfoxide) at 37° C. for 2 minutes, then with merthiolate (sodium ethylmercurithiosalicylate; 40 μM) for 2 minutes, and thereafter with FMLP (formyl-methionyl-leucylphenylalanine; $10^{-7}$ M) for 15 minutes. After solid phase extraction the metabolites of arachidonic acid 5-HETE, $LTB_4$, 6-trans-$LTB_4$-isomers, 20-OH-$LTB_4$ and 20-COOH-$LTB_4$ were identified by RP-HPLC [M. Haurand and L. Flohé in Biochem. Pharmacol. 38, 2129-37 (1989)].

To examine the reversibility of the inhibitory action the cells were incubated with a compound according the invention or a solvent (ethanol and/or dimethyl sulfoxide) at 37° C. for 5 minutes, centrifuged at $300 \times g$ for 5 minutes and resuspended in 2 ml HBSS. Then the cells were incubated with merthiolate (40 μM) at 37° C. for 2 minutes and thereafter with FMLP ($10^{-7}$ M) for 15 minutes. The $IC_{50}$-value of the reversible inhibitory action was 2μmolar when the compound prepared according to Example 1 was used.

Inhibition of 12-HETE- and 5S,12S-DiHETE-Synthesis Induced by FMLP/Merthiolate of Human Polymorphonuclear Leukocytes and Thrombocytes Coincubations of human granulocytes and thrombocytes were carried out and investigated according to the inhibition of leukotriene-synthesis induced by FMLP/merthiolate. 12-HETE and 5S,12S-dihydroxy-HETE (5S,12S-DiHETE) were additionally included in the evaluation. The compound prepared according to Example 1 did not exert an inhibitory action on 12-lipoxygenase.

Inhibition of Cyclooxygenase

Sheep seminal vesicle microsomas (80 μg protein/ml buffer; 50 mM potassium phosphate buffer of pH 7.4) in 1 ml aliquots were incubated with arachidonic acid (20 μM; 150,000 dpm; $1-^{14}C$) and either with a Compound according to the invention (0.1 to 100 μM) or with a solvent (ethanol and/or dimethyl sulfoxide) at 20° C. for 15 minutes. After addition of acetic acid and extraction with ethyl acetate, the metabolites of arachidonic acid were separated by thin layer chromatography into a fraction containing prostaglandins and a fraction containing arachidonic acid. The distribution of the different $^{14}C$-labelled fractions was measured using a TLC linear analyzer. By correlating the percentages of the amount of the product formed under the action of cyclooxygenase in the presence of solvent and in the presence of different concentrations of compounds according to the invention, the $IC_{50}$-values of the compounds prepared according to Examples 1, 3 and 5 were found to be >500 μM, thereby indicating that none of the test substances had an inhibiting effect on cyclooxygenate.

Inhibition of Thromboxane Synthase

After addition of prostacyclin, human thrombocytes were isolated from platelet-rich plasma and suspended in Tyrode-Hepes buffer of pH 7.4 at $2 \times 10^8$ cells/ml.

One ml aliquots of cells were incubated either with a compound according to the invention (0.1 to 100 μM) or a solvent (ethanol and/or dimethyl sulfoxide) at 37° C. for 3 minutes and thereafter with radioactively labelled arachidonic acid (3.5 μM) for 5 minutes. The reaction was stopped and the metabolites of arachidonic acid were extracted by adding methanol, chloroform and formic acid. After evaporation of the chloroform-containing layer to dryness under nitrogen, the residue obtained was resuspended in 50 μl chloroform and analyzed by thin layer chromatography. The distribution of the radioactivity of the different metabolites of arachidonic acid was measured using a TLC linear analyzer. By correlating the percentages of the amount of $TXB_2$ formed under the action of thromboxane synthase in the presence of solvent and in the presence of different concentrations of compounds according to the invention, the following $IC_{50}$-values were determined graphically from semilogarithmic diagrams.

| Compound According to Example No. | $IC_{50}$-Value [μm] |
| --- | --- |
| 1 | 2.8 |
| 3 | 2.9 |
| 5 | 2.5 |
| Comparison Zileuton (A 64 077) | 4.0 >100 |
| 4-[2-(1H-imidazol-1-yl)-ethoxy]benzoic acid hydrochloride (UK 37 248) | 2.7 |

The compounds of the invention prepared according to Examples 1, 3 and 5 have the same inhibitory potency as the hydrochloride of the imidazolylethoxybenzoic acid UK 37 248 which inhibits the activity of thromboxane synthase but not the activity of 5-lipoxygenase. The 5-lipoxygenase inhibitor Zileuton (A 64 077) did not exert an inhibitory action on thromboxane synthase.

Allergen-Induced Bronchoconstriction in Guinea Pigs (Konzett-Roessler)

The antiasthmatic effect of compounds according to the invention was tested in anesthetized and ventilated guinea pigs. To induce an asthmatic reaction, the animals were passively sensitized by a single intraperitoneal injection of anti-ovalbumin serum. After 48 hours an asthmatic reaction was elicited by intravenous challenge with 0.2 mg/kg of ovalbumin. The immediately resulting bronchoconstriction was measured as an increase in intratracheal pressure. Effects caused by histamine, serotonin and sympathic counterreaction were eliminated by intravenous pretreatment with 2.15 mg/kg of mepyramine, 46.4 μg/kg of propranolol, 4.64 mg/kg of atropine, and 1 mg/kg of methysergide, all administered 5 minutes before challenge. Compounds according to the invention were orally administered 60 minutes before the administration of ovalbumin. The following ED40-values for the inhibition of the bronchoconstriction elicited by ovalbumin, i.e. the effective doses causing a 40% average inhibition of the bronchoconstriction, were determined:

| Compound According to Example No. | $ED_{50}$-Value [mg/kg] |
| --- | --- |
| 1 | 9.3 |
| 2 | 5.1 |
| 3 | 15.5 |
| 4 | 6.3 |

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations falling within the scope of the appended claims and equivalents thereof.

What we claim is:

1. A 3- or 4- (1H-imidazol-1-yl) phenol compound corresponding to the formula I

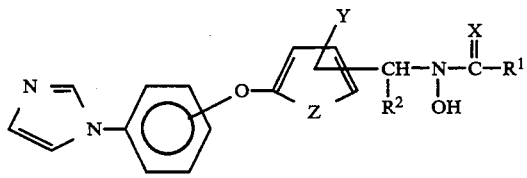

wherein
$R^1$ represents $NH_2$ or $CH_3$,
$R^2$ represents H or $CH_3$,
X represents O or S,
Y represents H, OH or $OCH_3$, and
Z represents —CH=CH—, O or S, or a pharmaceutically acceptable salt thereof.

2. A compound according to claim 1, wherein $R^2$ is H.

3. A compound according to claim 1, wherein Z is —CH=CH—.

4. A compound according to claim 1, wherein Z is O.

5. A compound according to claim 1, wherein Z is S.

6. A compound according to claim 1, selected from the group consisting of N-hydroxy-N-[4-[4-(1H-imidazol-1-yl)phenoxy]phenylmethyl]urea and the corresponding imidazolium chloride.

7. A compound according to claim 1, selected from the group consisting of N-hydroxy-N-[4-[4-(1H-imidazol-1-yl)phenoxy]phenylmethyl]acetamide and pharmaceutically acceptable salts thereof.

8. A compound according claim 1, selected from the group consisting of N-hydroxy-N-{3-[4-(1H-imidazol-1-yl)phenoxy]phenylmethyl}urea, N-hydroxy-N-{3-[4-(1H-imidazol-1-yl)phenoxy]-6-methoxy-phenylmethyl}urea, N-hydroxy-N-{4-[4-(1H-imidazol-1-yl)phenoxy]phenylmethyl}thiourea, N-hydroxy-N-{4-[3-(1H-imidazol-1-yl)phenoxy]phenylmethyl}urea and pharmaceutically acceptable salts thereof.

9. A compound according to claim 1, selected from the group consisting of N-hydroxy-N-{1-[4-[i4-(1H-imidazol-1-yl)phenoxy]phenyl]ethyl}urea and pharmaceutically acceptable salts thereof.

10. A compound according to claim 1, selected from the group consisting of N-hydroxy-N-{5-[4-(1H-imidazol-1-yl)phenoxy]furan-2-yl-methyl}urea and pharmaceutically acceptable salts thereof.

11. A compound according to claim 1, selected from the group consisting of N-hydroxy-N-{5-[4-(1H-imidazol-1-yl)phenoxy]thien-2-yl-methyl}urea and pharmaceutically acceptable salts thereof.

12. A pharmaceutical composition comprising an effective 5-lipoxygenase and thromboxane synthase inhibiting amount of at least one 3- or 4-(1H-imidazol-1-yl)phenol compound according to claim 1 and a pharmaceutically acceptable carrier, diluent or solvent.

13. A pharmaceutical composition according to claim 12, for topical, inhalative or parenteral administration.

14. A pharmaceutical composition according to claim 12, for oral administration.

15. A method of treating a patient suffering from a disorder attributable to the action of leukotrienes and thromboxane A2, said method comprising administering to said patient an effective 5-lipoxygenase and thromboxane synthase inhibiting amount of at least one compound according to claim 1.

16. A method of treating a patient suffering from asthma comprising administering to said patient an effective anti-asthma amount of at least one compound according to claim 1.

* * * * *